United States Patent [19]

Lele

[11] Patent Number: 4,938,216
[45] Date of Patent: Jul. 3, 1990

[54] MECHANICALLY SCANNED LINE-FOCUS ULTRASOUND HYPERTHERMIA SYSTEM

[75] Inventor: Padmakar P. Lele, Winchester, Mass.

[73] Assignee: Massachusetts Institute of Technology, Cambridge, Mass.

[21] Appl. No.: 209,519

[22] Filed: Jun. 21, 1988

[51] Int. Cl.$^5$ .............................................. A61N 5/00
[52] U.S. Cl. ................................. 128/399; 128/24 A; 73/642
[58] Field of Search ................ 128/399, 24 A, 660.03, 128/660.09, 663.01; 73/642, 618

[56] References Cited

U.S. PATENT DOCUMENTS

| | | | |
|---|---|---|---|
| 4,397,314 | 8/1983 | Vaguine | 128/399 |
| 4,441,486 | 4/1984 | Pounds | 128/24 A |
| 4,459,852 | 7/1984 | Chubachi et al. | 73/642 X |
| 4,549,533 | 10/1985 | Cain et al. | 128/24 A |
| 4,556,070 | 12/1985 | Vaguine et al. | 128/804 |
| 4,586,512 | 5/1986 | Do-huu et al. | 128/660 |
| 4,620,546 | 11/1986 | Aida et al. | 128/660 |
| 4,622,972 | 11/1986 | Giebeler, Jr. | 128/399 |
| 4,646,756 | 3/1987 | Watmough et al. | 128/804 |
| 4,708,127 | 11/1987 | Abdelghani | 128/24 A |

FOREIGN PATENT DOCUMENTS 0214782  3/1987  European Pat. Off. .... G10K/11/34

OTHER PUBLICATIONS

Lele, P. P., 1975, "Hyperthermia by Ultrasound", Proceedings of the International Symposium on Cancer Therapy by Hyperthermia and Radiation, American College of Radiology, Washington, D.C., pp. 168–178.

Lele, P. P., 1981, "An Annular-Focus Ultrasonic Lens for Production of Uniform Hyperthermia in Cancer Therapy", Ultrasound in Medicine and Biology, pp. 191–193.

Lele, P. P., 1983, "Physical Aspects and Clinical Studies with Ultrasonic Hyperthermia", Hyperthermia in Cancer Therapy, G. K. Hall and Co., pp. 333–367.

Sleefe, G. E. and Lele, P. P., 1985, "Phased Arrays for the Induction of Local Hyperthermia", Proceedings of the IEEE 1985 Ultrasonics Symposium.

Lele, P. P., 1986, "Rationale, Technique and Clinical Results with Scanned, Focused Ultrasound (SIMFU) System", IEEE Eighth Annual Conference of the Engineering in Medicine and Biology Society.

Lele, P. P., 1987, "Ultrasound: Synergistic Effects and Application in Cancer Therapy by Hyperthermia", Ultrasound, Plenum Publishing Corporation, pp. 307–332.

Lele, P. P., 1987, "Effects of Ultrasound on 'Solid' Mamalian Tissues and Tumors in Vivo", "Ultrasound", Plenum Publishing Corporation, pp. 275–306.

Lele, P. P. and J. Goddard, 1987, "Optimizing Insonation Parameters in Therapy Planning for Deep Heating by SIMFU", IEEE Ninth Annual Conference of the Engineering in Medicine and Biology Society.

Lele, P. P., Goddard, J. Blanter, M., 1987, "Clinical Results with Scanned, Intensity-Modulated, Focused Ultrasound (SIMFU) System", Proceedings of 73rd Annual Meeting, Radiological Society of North America, pp. 157–170.

Primary Examiner—Lee S. Cohen
Attorney, Agent, or Firm—Thomas J. Engellenner; David A. Jacobs

[57] ABSTRACT

A therapeutic hyperthermia system generates a line-focus beam of ultrasound which can be mechanically scanned across a treatment volume of tissue. The ultilization of a line-focus advantageously reduces the peak intensity of the ultrasonic beam. The system includes methods of scanning the line-focus beam to provide optimal treatment protocols for deep tumors and other pathological conditions while minimizing damage in overlying body tissues. The utilization of mechanical scanning reduces the number of transducers, amplifiers and associated electronics required.

10 Claims, 2 Drawing Sheets

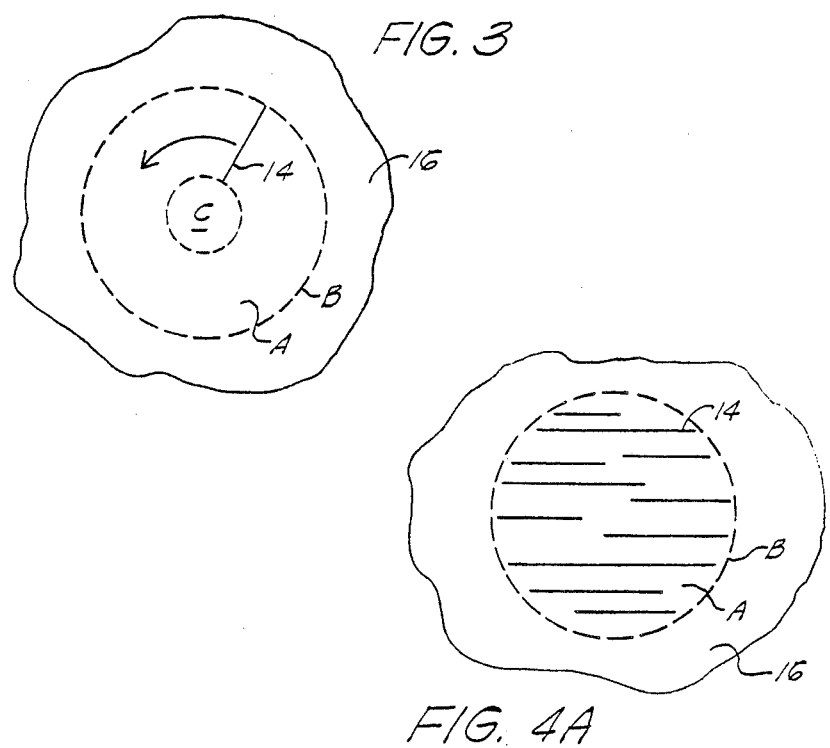
FIG. 3
FIG. 4A
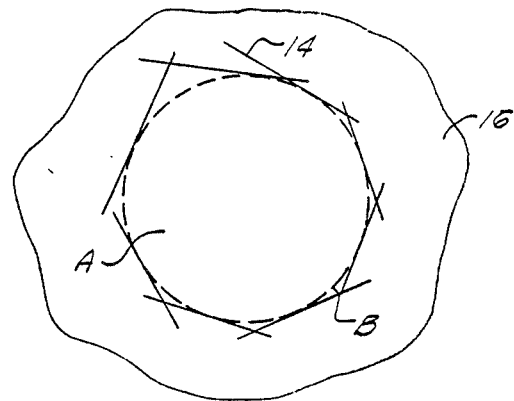
FIG. 4B

MECHANICALLY SCANNED LINE-FOCUS ULTRASOUND HYPERTHERMIA SYSTEM The U.S. Government has rights in this invention pursuant to Contract Number CA 31303-03 awarded by the Nation Cancer Institute.

BACKGROUND OF THE INVENTION

This invention relates generally to systems for ultrasound hyperthermia, and, more particularly, relates to apparatus and methods for delivering ultrasonic energy in hyperthermic treatment of internal cancers and other diseases which respond to temperature elevation.

Production of a controllable level of temperature elevation or hyperthermia at pre-selected locations and volumes of tissue has been found to be of significant therapeutic value in the treatment of patients with cancer or other diseases. Several methods utilizing focused ultrasound to produce such hyperthermia have been described in the art. See, for example, the following publications:

Lele, P. P., 1975, "Hyperthermia by Ultrasound," Proceedings of the International Symposium on Cancer Therapy by Hyperthermia and Radiation, American College of Radiology, Washington, D.C., pp. 168–178;

Lele, P. P., 1981, "An Annular-Focus Ultrasonic Lens for Production of Uniform Hyperthermia in Cancer Therapy", Ultrasound in Medicine and Biology, pp. 191–193;

Lele, P. P., 1983, "Physical Aspects and Clinical Studies with Ultrasonic Hyperthermia," Hyperthermia in Cancer Therapy G. K. Hall and Co, pp. 333–367;

"Phased Arrays for the Induction of Local Hyperthermia," Proceedings of the IEEE 1985 Ultrasonics Symposium;

Lele, P. P., 1986, "Rationale, Technique and Clinical Results with Scanned, Focused Ultrasound (SIMFU) System," IEEE Eighth Annual Conference of the Engineering in Medicine and Biology Society;

Lele, P. P., 1987, "Ultrasound: Synergistic Effects and Application in Cancer Therapy by Hyperthermia," Plenum Publishing Corporation;

Lele, P. P., 1987, "Effects of Ultrasound on Solid' Mammalian Tissues and Tumors In Vivo," Plenum Publishing Corporation; and Lele, P. P. and J. Goddard, 1987, "Optimizing Insonation Parameters in Therapy Planning for Deep Heating by SIMFU," IEEE Ninth Annual Conference of the Engineering in Medicine and Biology Society.

Further, the following U.S. patents disclose examples of recent developments in the hyperthermia field:

U.S. Pat. No. 4,441,486, Pounds
U.S. Pat. No. 4,549,533, Cain et al
U.S. Pat. No. 4,586,512, Do-huu et al
U.S. Pat. No. 4,622,972, Giebeler, Jr.

The Pounds patent discloses a hyperthermia system including a plurality of transducers mounted in an isospherical configuration. Each transducer is configured so that its compressional mode of vibration is suppressed near the center.

The Cain et al patent discloses ultrasound generating apparatus having a plurality of side-by-side tapered piezoelectric transducer elements. Means are provided for energizing the transducer elements with electrical energy having a frequency which is varied to modulate the ultrasound produced by the transducer elements.

The Do-huu et al patent discloses an emitter which focuses ultrasonic radiation into biological tissues for producing localized heating. The radiation emitter consists of a piezoelectric plate subdivided into annular radiating zones of equal width by a set of concentric circular grooves.

The Giebeler, Jr. patent discloses an ultrasound hyperthermia applicator comprising a plurality of transducers which can be operated in different grouping modes. The beams from these elements can be individually focused according to a spiral or multi-spiral focusing scheme, in an attempt to provide uniform heating, without scanning, of a volume greater than the inherent focal size of the individual transmitter elements.

Additionally, European Patent Application Ser. No. 214,782 of Umemura et al discloses a transducer composed of a plurality of elements divided at least in a circumferential direction. The phases of drive signals may be changed according to the respective positions of the oscillating elements, to form an annular focal zone having a variable radius.

Certain conventional systems for ultrasonically induced hyperthermia utilize one or more mechanically or electromechanically scanned, conically convergent spot-focus beams of ultrasound, produced by radially symmetric, high gain acoustic lenses. Such spot-focus lenses concentrate ultrasonic energy in a small spot in which high peak levels of ultrasound intensity are generated.

When employed in the production of therapeutic hyperthermia, conventional spot-focus beam systems suffer from a number of deficiencies. In particular, peak intensities delivered to the target tissue must be kept below the level at which irreversible damage can result through cavitation or excessive heating. The high gain of spot focus lenses therefore severely restricts the total amount of power which can be delivered to the treatment volume for heating to a safe therapeutic temperature.

Additionally, in conventional spot-focus systems, energy delivery is concentrated within the focal volume, which is generally much smaller than the treatment volume. Sustained and uniform heating of the entire treatment volume therefore requires that the spot-focus beam be moved throughout the treatment volume in closely-spaced trajectories, within a period of approximately 1 to 5 seconds. Conventional spot-focus hyperthermia systems typically cannot provide these scan speeds on a sustained basis, resulting in inadequate and non-uniform heating of the tissues in the treatment volume.

Accordingly, there exists a need for hyperthermia methods and apparatus which permit the delivery of high overall levels of ultrasonic energy while eliminating high peak intensities, and which provide high scan speed and enhanced uniformity of heating throughout the treatment volume.

It is accordingly an object of the invention to provide improved ultrasound hyperthermia apparatus.

It is another object of the invention to provide ultrasound hyperthermia apparatus which delivers high overall levels of ultrasonic energy while eliminating high peak intensities.

It is a further object of the invention to provide ultrasound hyperthermia apparatus which produces uniform heating of the treatment volume.

Other general and specific objects of the invention will in part be obvious and will in part appear hereinafter.

SUMMARY OF THE INVENTION

The foregoing objects are attained by the invention, which provides an ultrasonic hyperthermia system for delivering hyperthermic therapy to a subject. In accordance with one aspect of the invention, the system includes a piezoelectric transducer element which can produce a beam of ultrasonic energy upon electrical activation, in combination with electrical activation elements for activating the transducer element.

The invention further includes a line-focus lens element for focusing a beam of ultrasonic energy from the transducer element into a line-focus, and a scanning module for scanning the line-focused beam across a target region of a subject.

In accordance with another aspect of the invention, the electrical activation elements further include adjustment elements for varying the electrical excitation and, as a result, the intensity of the ultrasonic energy beam.

In a further aspect of the invention, the line-focus lens element is a cylindrical lens, and the scanning module includes elements for providing non-linear scanning. These non-linear scanning elements can include rotational elements for rotating the line-focused beam to provide non-linear scanning.

The invention also provides a scanning module which includes translational elements for changing the focal depth within the tissue as the line-focused beam is rotated.

The invention accordingly comprises apparatus embodying features of construction, combinations of elements and arrangements of parts, as exemplified in the following detailed disclosure, and the scope of the invention is indicated in the claims.

BRIEF DESCRIPTION OF THE DRAWINGS

For a fuller understanding of the nature and objects of the invention, reference should be made to the following detailed description and the accompanying drawings, in which:

FIG. 3 depicts a scanning pattern which can be generated by the system of FIG. 1; and FIG. 4 depicts other scanning patterns which can be generated by the system of FIG. 1.

DESCRIPTION OF PREFERRED EMBODIMENTS

Figure 1:
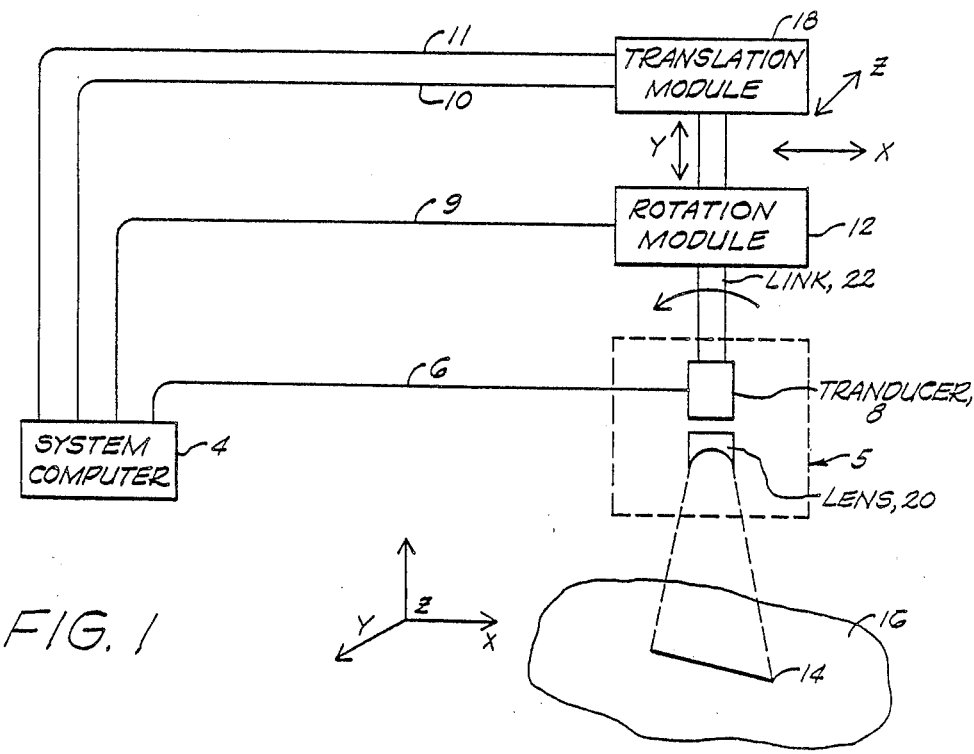
FIG. 1 is a schematic diagram depicting a mechanically scanned line-focus ultrasound hyperthermia system according to the invention.

FIG. 1 depicts a mechanically scanned line-focus ultrasound hyperthermia system according to the invention. The illustrated hyperthermia system 2 includes a system computer 4 of conventional design and programming and an ultrasound generation module 5, for generating a line-focus beam 14 and directing the beam 14 into tissue 16. Those skilled in the art will appreciate that mechanical controls, such as potentiometers, can be substituted for system computer 4.

As FIG. 1 illustrates, system computer 4 can generate variable activation signals 6. These signals are transmitted to transducer 8 contained in diffuse focus ultrasound generation module 5. Transducer 8 responds to the activation signals 6 in a manner known in the art, to generate ultrasonic energy. This energy is focused by lens 20, in a manner discussed in greater detail below in connection with FIG. 2, to form a line-focus beam 14. In a preferred embodiment of the invention, system computer 4 can vary the amplitude of activation signals 6 so as to vary the intensity and focal dimensions of the line-focus beam 14.

When the invention is practiced in a hyperthermia therapy setting, ultrasound generating module 5 is connected by coupling 22 to linked translation module 18 and rotation module 12. These position control modules preferably contain stepper motors or servos of conventional design and construction.

As FIG. 1 illustrates, the ultrasound generating module 5 can be eccentrically mounted to rotation module 12 by means of link 22. Rotation module 12, in turn, can be actuated and controlled by angular position signals 9 generated by system computer 4, for rotating ultrasound generating module 5 through a selected orbital path. As a result of this rotation and eccentric placement, the treatment volume 16 is scanned by the line-focus beam 14. Moreover, the diameter of the heated field can be more than twice the length of a single line-focus 14, depending upon the eccentricity of the orbit of ultrasound generating module 5.

Additionally, as shown in FIG. 1, system computer 4 can assert X-Y position control signals 10 and Z-axis position control signals 11 to the inputs of translation module 18. Translation module 18 reads the position control signals asserted by system computer 4 and responds by actuating and controlling translational motion of ultrasound generating module 5.

Figure 2:
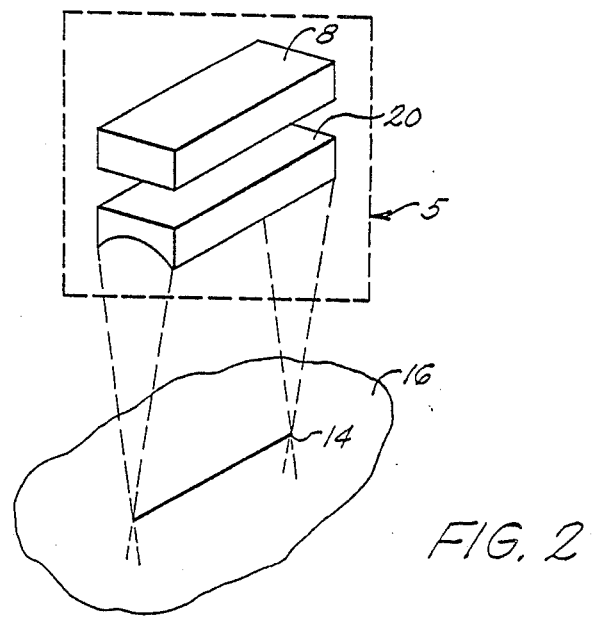
FIG. 2 depicts a transducer and lens module utilized in connection with the system of FIG. 1.

FIG. 2 depicts a transducer 8 and cylindrical lens 20 which form an ultrasound generation module 5 utilized in connection with the system of FIG. 1. As shown in FIG. 2, the transducer 8 has a substantially constant thickness along its long axis. The cylindrical acoustic lens 20 generates a line-focus beam 14, rather than the spot-focus beam generated by certain prior art systems. The length of the line 14 is substantially equal to that of the transducer 8. The ultrasound energy generated by transducer 8 is thus distributed over the entire length of the line 14, which lies in a plane perpendicular to the direction of energy propagation and parallel to the major axis of lens 20. The peak intensity in the focal region is therefore reduced by approximately one order of magnitude, relative to that produced by a spot-focus ultrasound beam, depending on the length of the line-focus and the ultrasonic frequency employed. This reduction in peak intensity enables the utilization of proportionately higher power levels without the danger of tissue damage.

Moreover, because the use of a line-focus lens 20 reduces the effective aperture of the system as compared with that of a spot-focus lens, the focal region is also elongated in the direction of energy propagation, thus heating a greater thickness of the tissue 16.

Conventional hyperthermia systems utilizing spot-focused transducers typically concentrate ultrasound energy, producing excessive heating in the center of the target area and lower temperatures at the periphery This focal concentration creates problems of tissue overheating and cavitation. In one embodiment of the invention, therefore, to prevent greater heating at the inner radii, a scan pattern is selected such that time-averaged energy delivery is substantially equalized throughout the target volume, as discussed in greater detail below in connections with FIGS. 3 and 4.

Additionally, in a preferred embodiment of the invention, the output of the transducer at the inner radii can be reduced by apodization or "amplitude shading." In particular, those skilled in the art will appreciate that apodization involves activating the transducer element so that relatively greater power is delivered to the periphery of the target area, and relatively less power is delivered to the center of the target area. This variable activation eliminates or reduces overheating of the center of the target area.

The invention can also be practiced in an embodiment in which central heating is reduced by the use of ultrasound absorptive materials placed in front of the lens 20.

The heating pattern depicted in FIG. 3, generated by appropriate angular position signals 9 transmitted from system computer 4 to rotation module 12 (illustrated in FIG. 1), has been found to produce excellent heating uniformity without excessive central heating. In particular, FIG. 3 depicts a preferred heating pattern applied to a target area A in tissue 16. Target area A is bounded by a substantially circular boundary B, and is rotationally scanned by line-focus beam 14 which can be swept in the indicated direction of rotation.

The length of line-focus beam 14 is less than the radius of the target area A, so that a central "hole" C in the heating pattern is created. This central "hole" C in the heating pattern substantially reduces the possibility of overheating the central region of the target area A, and promotes uniform heating of the target area.

Additionally, sweeping the beam 14 through an arc as depicted in FIG. 3 produces uniform heating at greater depths, because the beam 14 is constantly in motion, and there is no overlap of the ultrasound beam 14 as the angular position of the beam 14 changes. Moreover, the system illustrated in FIGS. 1 and 2 can be utilized with an effective aperture of reduced dimensions, thereby providing a greater depth of field and enhanced uniformity.

In accordance with the invention, complex heating patterns can be generated by combining X, Y, and Z axis translational motions, actuated and controlled by translation module 18, with the rotation generated by rotation module 12. Thus, in a preferred practice of the invention, system computer 4 can assert appropriate motion control signals to translation module 18 and rotation module 12, thereby generating heating patterns like those shown in FIG. 4. The heating pattern depicted in FIG. 4 are characterized by a substantially uniform distribution of applied energy across the target area, without excess heating of the central region.

Those skilled in the art will appreciate that a significant advantage of the invention lies in its ability to reduce the peak intensity of the ultrasonic energy by adjustably producing a line-focus. In particular, the invention provides a hyperthermia system in which even a single ultrasound transducer can deliver ultrasonic energy more uniformly through a large tissue volume than would be possible with a plurality of mechanically or electrically scanned spot-focused transducers. Additionally, by utilizing mechanical scanning, the number of transducers, amplifiers and associated electronics is reduced, while simplicity and scan speed are enhanced.

It will thus be seen that the invention efficiently attains the objects set forth above, among those made apparent from the preceding description. In particular, the invention provides a mechanically scanned line-focus ultrasonic hyperthermia system capable of heating both deep and irregularly shaped tumors, and which delivers enhanced levels of total power while eliminating high peak intensities.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. An ultrasonic hyperthermia system for delivering hyperthermic therapy to a subject, the system comprising a piezoelectric transducer element which can produce a beam of ultrasonic energy upon electrical activation, said piezoelectric transducer element having a selected length and a substantially constant thickness over said length;

a line-focus lens element coupled with the transducer element and adapted to be situated between the transducer element and the subject, for focusing a beam of ultrasonic energy produced by said transducer element upon electrical activation into a substantially linear focal region, said substantially linear focal region having a length substantially equal to the length of the transducer element;

electrical activation means for activating the transducer element, the electrical activation means including adjustment means for selectively varying the electrical excitation, and, as a result, the intensity of the ultrasonic energy beam, the adjustment means including means for selectively varying the intensity of the ultrasonic energy beam continuously across the substantially linear focal region; and scanning means for scanning the line-focused beam across a target region of a subject during activation of the transducer element.

2. The system of claim 1 wherein the line-focus lens element is a cylindrical lens.

3. An ultrasonic hyperthermia system for delivering hyperthermic therapy to a subject, the system comprising a piezoelectric transducer element which can produce a beam of ultrasonic energy upon electrical activation;

a line-focus lens element coupled with the transducer element and adapted to be situated between the transducer element and the subject, for focusing a beam of ultrasonic energy produced by said transducer element upon electrical activation into a substantially linear focal region;

electrical activation means for activating the transducer element, the electrical activation means including adjustment means for selectively varying the electrical excitation, and, as a result, the intensity of the ultrasonic energy beam, the adjustment means including means for selectively varying the intensity of the ultrasonic energy beam continuously across the substantially linear focal region; and scanning means for scanning the line-focused beam across a target region of a subject during activation of the transducer element, the scanning means including means for scanning the ultrasonic energy beam across said target region in a non-linear pattern.

4. The system of claim 3 wherein the means for scanning in a non-linear pattern includes a rotational means for rotating the line-focused beam to provide non-linear scanning.

5. The system of claim 4 wherein the scanning means further includes translational means for changing the focal depth within the tissue as the line-focused beam is rotated.

6. An ultrasonic hyperthermia method for delivering hyperthermic therapy to a subject, the method comprising the steps of:

configuring a piezoelectric transducer element to have a selected length and a substantially constant thickness over said length and to produce a beam of ultrasonic energy upon electrical activation;

orienting a line-focus lens element to focus a beam of ultrasonic energy produced by said transducer element upon activation into a substantially linear focal region having a length substantially equal to the length of the transducer element;

electrically activating the transducer element to produce the beam of ultrasonic energy, the activating step including the step of selectively varying the electrical activation, and as a result, the intensity of the ultrasonic energy beam, the varying step including the step of selectively varying the intensity of the ultrasonic energy beam continuously across the substantially linear focal region; and scanning the line-focused beam across a target region of a subject during activation of the transducer element.

7. The method of claim 6 wherein the orienting step includes the step of orienting a cylindrical lens to focus the beam into a line-focus.

8. An ultrasonic hyperthermia method for delivering hyperthermic therapy to a subject, the method comprising the steps of:

configuring a piezoelectric transducer element to produce a beam of ultrasonic energy upon electrical activation;

orienting a line-focus lens element to focus a beam of ultrasonic energy produced by said transducer element upon activation into a substantially linear focal region;

electrically activating the transducer element to produce the beam of ultrasonic energy, the activating step including the step of selectively varying the electrical activation, and as a result, the intensity of the ultrasonic energy beam, the varying step including the step of selectively varying the intensity of the ultrasonic energy beam continuously across the substantially linear focal region; and scanning the line-focused beam across a target region of a subject during activation of the transducer element, the scanning step including the step of scanning the line-focus beam in a non-linear scanning pattern.

9. The method of claim 8 wherein the scanning step further includes the step of rotating the line-focused beam to provide non-linear scanning.

10. The method of claim 9 wherein the scanning step further includes the step of translating the line-focused beam for changing the focal depth within the tissue as the line-focused beam is rotated.

* * * * *